United States Patent
Perrott et al.

(10) Patent No.: US 9,385,747 B1
(45) Date of Patent: Jul. 5, 2016

(54) CAPACITANCE-TO-DIGITAL CONVERTER UTILIZING DIGITAL FEEDBACK AND AUXILIARY DAC

(71) Applicant: Silicon Laboratories Inc., Austin, TX (US)

(72) Inventors: Michael H. Perrott, Nashua, NH (US); Louis Nervegna, Andover, MA (US)

(73) Assignee: Silicon Laboratories Inc., Austin, TX (US)

(*) Notice: Subject to any disclaimer, the term of this patent is extended or adjusted under 35 U.S.C. 154(b) by 0 days.

(21) Appl. No.: 14/575,167

(22) Filed: Dec. 18, 2014

(51) Int. Cl.
  *H03M 3/00* (2006.01)

(52) U.S. Cl.
  CPC .............. *H03M 3/362* (2013.01); *H03M 3/464* (2013.01); *H03M 3/476* (2013.01); *H03M 3/496* (2013.01)

(58) Field of Classification Search
  CPC ..... H03M 3/362; H03M 3/464; H03M 3/496; H03M 3/476
  USPC .................................. 341/172, 155, 144, 143
  See application file for complete search history.

(56) References Cited

U.S. PATENT DOCUMENTS

| | | | |
|---|---|---|---|
| 5,801,307 A | 9/1998 | Netzer | |
| 5,974,895 A | 11/1999 | Steger et al. | |
| 6,861,879 B2 | 3/2005 | Gupta | |
| 6,924,760 B1* | 8/2005 | McLeod | H03M 1/066 341/144 |
| 7,095,350 B2* | 8/2006 | Hagiwara | H03M 1/0665 341/143 |
| 7,315,200 B2 | 1/2008 | Holberg et al. | |
| 7,554,134 B2 | 6/2009 | Cummins | |
| 7,994,958 B2* | 8/2011 | Quiquempoix | H03M 3/34 341/143 |
| 8,007,167 B2 | 8/2011 | Cummins | |
| 8,145,175 B2 | 3/2012 | Miyano et al. | |
| 8,274,327 B2 | 9/2012 | Uchida | |
| 8,339,299 B2* | 12/2012 | Quiquempoix | H03M 1/0663 341/143 |
| 8,357,958 B2 | 1/2013 | Cummins | |
| 8,513,982 B1 | 8/2013 | Garrity et al. | |
| 2001/0020850 A1 | 9/2001 | McIntosh et al. | |
| 2006/0179943 A1 | 8/2006 | Willemin et al. | |
| 2007/0241798 A1 | 10/2007 | Masenas | |
| 2008/0094140 A1 | 4/2008 | Lim et al. | |
| 2008/0231290 A1 | 9/2008 | Zhitormirsky | |
| 2009/0284285 A1 | 11/2009 | Fagg | |

(Continued)

OTHER PUBLICATIONS

O'Connell, I. and Scanlan, T., "Sigma Delta Analog to Digital Converter for Use in a Remote Sensing Application," 2007 IEEJ International Analog VLSI Workshop, Nov. 7-9, 2007, Limerick Ireland, 5 pages.

*Primary Examiner* — Jean B Jeanglaude
(74) *Attorney, Agent, or Firm* — Abel Law Group, LLP

(57) ABSTRACT

A capacitance-to-digital converter circuit utilizes a capacitor bridge circuit to sense a difference in capacitance between sense capacitors and fixed capacitors in the bridge circuit. The sense capacitors vary according to a sensed parameter. Auxiliary capacitor digital to analog converters (DACs) are coupled to the capacitor bridge circuit to cancel the sensed difference. An analog to digital converter (ADC) receives a signal generated by the capacitor bridge circuit and the auxiliary capacitor DACs and converts the received signal to a digital signal. A digital accumulator accumulates the ADC output, whose output represents the difference in capacitance between the sense capacitors and the fixed capacitors. The accumulator output is used to control the auxiliary capacitor DACs to offset the difference in capacitance between the sense capacitors and the fixed capacitors. The accumulator output also provides the basis for the capacitance-to-digital circuit output.

21 Claims, 2 Drawing Sheets

(56) References Cited

U.S. PATENT DOCUMENTS

| | | |
|---|---|---|
| 2010/0201424 A1 | 8/2010 | Miyano et al. |
| 2010/0264751 A1 | 10/2010 | Lida et al. |
| 2010/0327819 A1 | 12/2010 | Macdougall |
| 2011/0215864 A1 | 9/2011 | Uchida |
| 2013/0285705 A1 | 10/2013 | Kabir et al. |
| 2014/0026642 A1 | 1/2014 | OConnell |
| 2014/0026652 A1 | 1/2014 | Cummins et al. |
| 2014/0146572 A1 | 5/2014 | Ye et al. |
| 2014/0375135 A1 | 12/2014 | Nervegna et al. |

* cited by examiner

US 9,385,747 B1

CAPACITANCE-TO-DIGITAL CONVERTER UTILIZING DIGITAL FEEDBACK AND AUXILIARY DAC

CROSS-REFERENCE TO RELATED APPLICATION(S)

This application relates to the applications entitled "Circuit Including a Switched Capacitor Bridge and Method," application Ser. No. 13/925,781, filed on Jun. 24, 2013, naming Louis Nervegna et. al., as inventors; and the application entitled "Capacitance to Digital Converter", application Ser. No. 13/954,955, filed on Jul. 30, 2013, naming Louis Nervegna et. al., as inventors, which applications are incorporated herein by reference.

BACKGROUND

1. Field of the Invention

This invention relates to capacitive-to-digital converters, and more particularly to capacitive-to-digital converters to sense a parameter using a bridge circuit.

2. Description of the Related Art

Capacitance-to-digital conversion plays an important role in many sensor applications such as measurement of pressure and humidity. In these sensing applications, key performance metrics include measurement range, resolution (i.e. rms noise of each measurement sample), accuracy, conversion time, area, and power consumption.

Due to the small size of capacitances that must be detected, analog amplifiers typically form a critical building block of capacitance-to-digital converters. These amplifiers often pose performance limitations due to their finite DC gain, nonlinear gain characteristic, and limited output swing. The finite DC gain and nonlinear gain characteristic of the amplifier can lead to nonlinearity in the capacitance-to-digital measurement characteristic, which degrades its accuracy performance. The limited output swing of the amplifier can lead to the need for a large area for the capacitance-to-digital converter in order to properly scale down voltage levels. Thus, improvements in capacitance-to-digital conversion are desirable.

SUMMARY OF EMBODIMENTS OF THE INVENTION

Accordingly, in an embodiment, the use of a digital feedback network reduces the impact of amplifier nonidealities on the performance of the capacitance-to-digital converter.

In one embodiment, a capacitance-to-digital converter circuit includes a capacitor bridge circuit to sense a difference in capacitance between one or more sense capacitors and other capacitors in the bridge circuit. Auxiliary capacitor digital to analog converters (DACs) are coupled to the capacitor bridge circuit to reduce the sensed difference observed at the output of the bridge circuit. An analog to digital converter (ADC) receives a signal generated by the capacitor bridge circuit and the auxiliary capacitor DACs and converts the received signal to a digital signal. A digital accumulator creates an accumulated digital signal based on the digital signal supplied by the ADC. The auxiliary capacitor DACs are controlled to offset a difference in capacitance between the one or more sense capacitors and the other capacitors in the bridge circuit based on the accumulated digital signal.

In another embodiment a method includes sensing a difference in capacitance between one or more sense capacitors and other capacitors in a capacitor bridge circuit. The sensed difference is offset using auxiliary capacitor digital-to-analog converters (DACs) coupled to the bridge circuit. An analog-to-digital converter (ADC) is coupled to the capacitor bridge circuit and the auxiliary capacitor DACs. The ADC generates a digital signal corresponding to the sensed difference as offset by the auxiliary capacitor DACs. A digital accumulator creates an accumulated digital signal, the accumulated digital signal corresponding to the sensed difference between the sense capacitors and other capacitors. The auxiliary capacitor DACs are controlled to offset the sensed difference based on the accumulated digital signal.

In another embodiment a capacitance-to-digital converter includes a capacitor bridge circuit including one or more first capacitors that vary according to a sensed parameter and second capacitors. The bridge circuit senses a difference in capacitance between the first capacitors and the second capacitors. One or more auxiliary capacitor digital-to-analog converters (DACs) are coupled to the capacitor bridge circuit to offset the difference in capacitance sensed by the capacitor bridge circuit. An analog-to-digital converter (ADC) is coupled to the capacitor bridge circuit and the one or more auxiliary capacitor DACs, the ADC is configured to supply a digital signal corresponding to a difference in capacitance sensed by the capacitor bridge circuit as offset by the one or more auxiliary capacitor DACs. A feedback capacitance is coupled to the digital signal from the ADC and the capacitor bridge circuit, with the digital signal from the ADC being responsive to a residual error caused by incomplete cancellation by the auxiliary capacitor DACs of the difference in capacitance between the first capacitors and the second capacitors in the bridge circuit. A digital feedback circuit includes a digital accumulator to accumulate the difference in capacitance sensed by the capacitor bridge circuit as offset by the one or more auxiliary capacitor DACs and supplies an accumulated signal indicative thereof. The accumulated signal corresponds to the difference in capacitance between the first capacitors and the second capacitors. The digital feedback path controls the auxiliary DACs to offset the difference between the first capacitors and the second capacitors based on the accumulated signal. The digital control path also supplies an output of the capacitance-to-digital converter based on the accumulated signal.

BRIEF DESCRIPTION OF THE DRAWINGS

The present invention may be better understood, and its numerous objects, features, and advantages made apparent to those skilled in the art by referencing the accompanying drawings.

DETAILED DESCRIPTION

Figure 1:
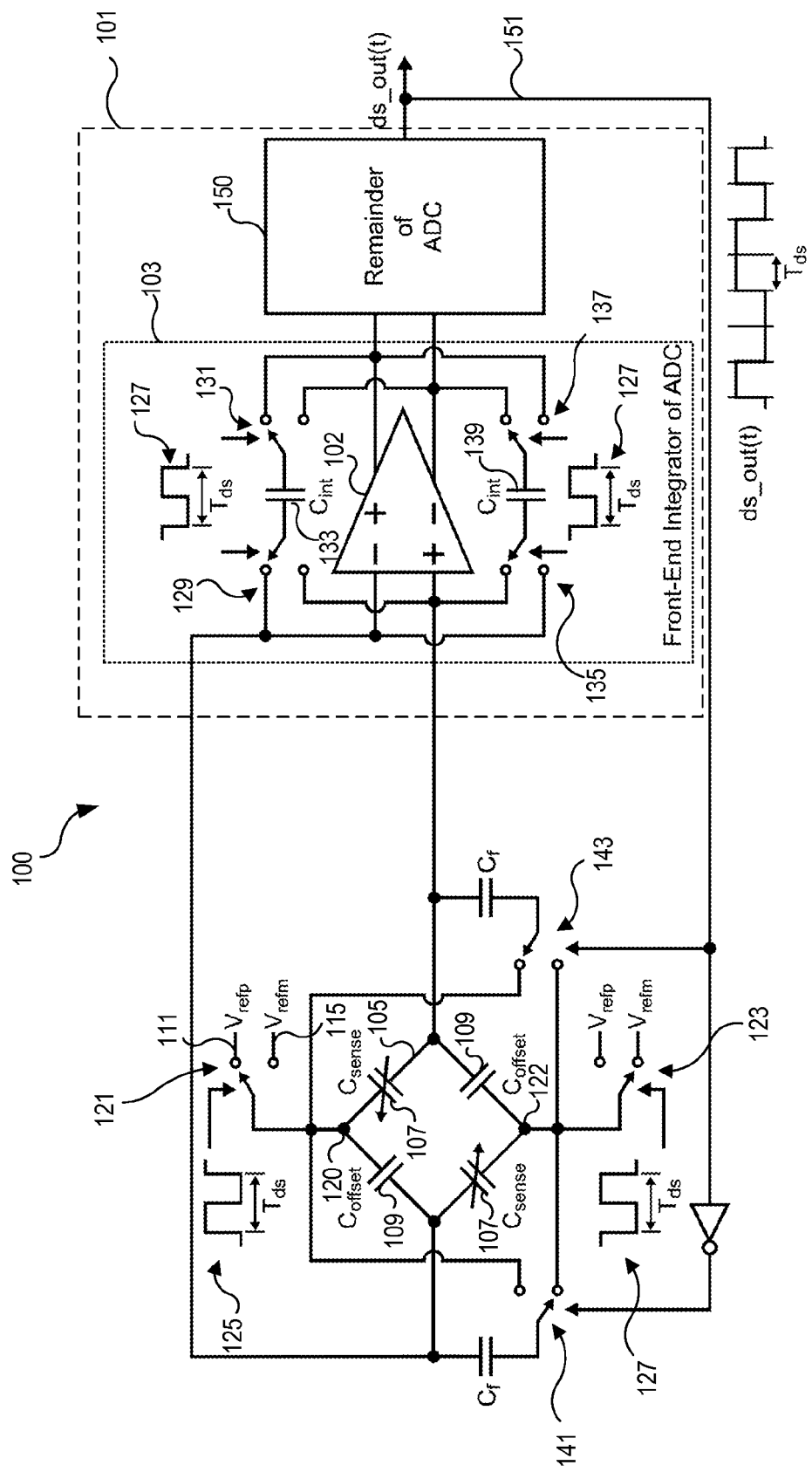
FIG. 1 illustrates a capacitance-to-digital converter utilizing a capacitive bridge network and a switched capacitor-based analog-to-digital converter, which includes an analog amplifier as part of its front-end integrator.

FIG. 1 illustrates capacitance-to-digital converter 100 that includes a switched capacitor based analog-to-digital converter (ADC) 101 that contains an analog amplifier 102 to realize its front-end integrator 103. The front-end integrator 103 rectifies and integrates signals received from capacitive bridge network 105. The illustrated capacitance-to-digital converter 100 has similarities to that contained in patent application entitled "Capacitance to Digital Converter" application Ser. No. 13/954,955, mentioned above. In the capacitive bridge 105, $C_{sense}$ capacitors 107 vary according to the sensed parameter (e.g., humidity or pressure) while $C_{offset}$ capacitors 109 are fixed.

The voltage on the top and bottom nodes 120 and 122 of the capacitor bridge 105 alternates between two reference voltages, a positive voltage reference $V_{refp}$ 111 and a negative reference voltage $V_{refm}$ 115, in order to generate charge transfer, $\Delta Q = +/-2(V_{refp} - V_{refm})(C_{sense} - C_{offset})$, into the front-end integrator 103 during each capacitor sample, where the sign of $\Delta Q$ alternates between plus and minus with period $T_{ds}$ corresponding to the clock signal 127. If $C_{sense} = C_{offset}$, the charge transferred into the front-end integrator is zero. The switches 121 and 123 are switched by the clock signal 127 (or its inverse 125) having a period of $T_{ds}$ to alternate the voltage supplied to the top and bottom nodes of the capacitor bridge 105.

In the front end integrator 103, the switches 129 and 131 alternately couple the integration capacitor $C_{int}$ 133 between the negative input and positive output or between the positive input and the negative output of amplifier 102. Similarly, the switches 135 and 137 alternately couple the integration capacitor 139 between the positive input and the negative output or between the negative input and positive output of amplifier 102. The integration capacitor switches are clocked by the clock signal 127. FIG. 1 shows the position of the various switches at the beginning of their associated clock cycle. The integration capacitor switches perform the function of alternating the placement of the $C_{int}$ capacitance within the front-end integrator, as shown in FIG. 1, in order to rectify the charge transfer $\Delta Q$ from the capacitor bridge 105. For example, assume that $\Delta Q$ has a waveform corresponding to a square wave being supplied by the capacitive bridge 105 and having an amplitude that corresponds to a difference in capacitance between the two sides of the bridge. In the illustrated embodiment, it is necessary to rectify the square wave so that the current into the integrator 103 accumulates according to the difference in capacitance. Without rectification, the alternating charge from each side of the bridge will cancel rather than accumulate over time.

The $C_{sense}$ capacitors change in response to the parameter (e.g., pressure or humidity) being measured. Thus, the charge $\Delta Q = +/-2(V_{refp} - V_{refm})(C_{sense} - C_{offset})$ transferred into the integrator 103 becomes nonzero as $C_{sense}$ changes to reflect the measured parameter. The rectified and accumulated value from integrator 103 is supplied to the remainder of the ADC 150. In an embodiment, the ADC is a second order delta sigma modulator where the integrator 103 is the first of two integrators forming the second order sigma delta modulator. Note that different ADCs may be used in various embodiments. The ADC illustrated in FIG. 1 generates an output ds_out(t) as a binary stream having an average value corresponding to the sensed parameter.

The rectified charge transfer to the front end integrator 103 is cancelled, on average, by charge transfer from the feedback capacitors, $C_f$, due to the fact that the ADC output dynamically varies the $C_f$ connection between $V_{refp}$ and $V_{refm}$ such that the average rectified charge transfer flowing into the front-end integrator becomes zero. Thus, the Delta Sigma output ds_out(t) 151 controls the switches 141 and 143 so that the feedback capacitors are coupled to the bridge circuit in a manner to cancel the charge transfer. Thus, the feedback capacitors $C_f$ account for any difference $C_{sense} - C_{offset}$. Thought of another way, the feedback capacitors function to offset the sensed parameter value that is being supplied by the ADC.

Note that the feedback capacitors, $C_f$, are connected directly to the bridge capacitance 105 nodes that feed into the frontend integrator 103 rather than through a switch, which avoids the negative impact of charge injection due to this switch. As such, the combined bridge and feedback capacitor network shown in FIG. 1 allows the use of low values of $C_f$ without concern for accuracy degradation of the capacitance-to-digital converter measurement performance due to such charge injection.

An important issue associated with ADCs is that the ADC utilizes amplifier circuits in both the front-end integrator as well as in the remaining ADC circuits. As is well known, large DC gain is often required of such amplifiers in order to achieve excellent accuracy and resolution performance. Also, a large $C_{int}$ may be required to achieve an acceptably low output swing. Finally, a simple amplifier implementation is desirable to save design time, reduce design risk, and facilitate a low area and power solution. Unfortunately, it can be difficult to meet each of these objectives with the capacitance-to-digital topology shown in FIG. 1.

Figure 2:
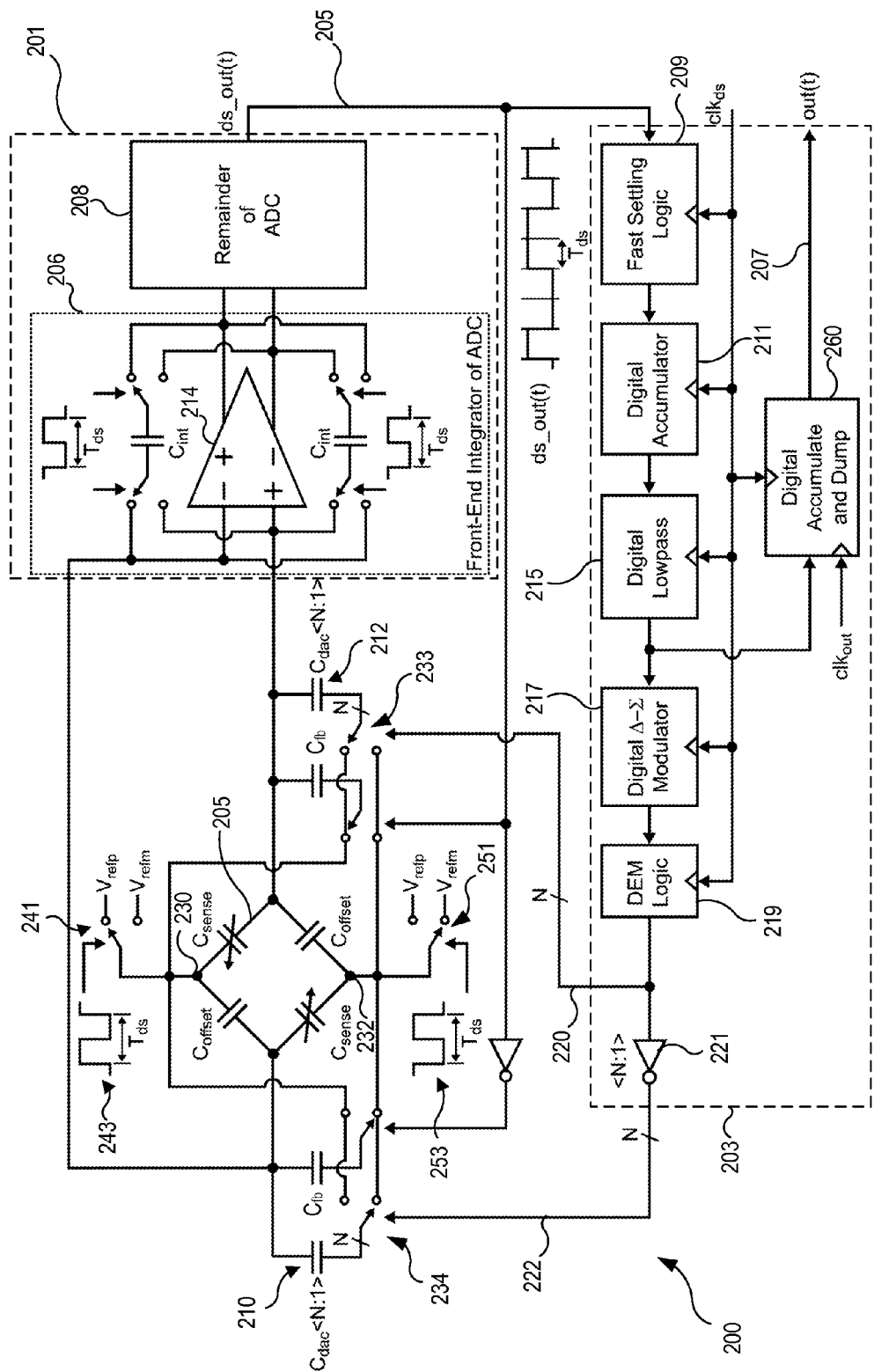
FIG. 2 illustrates an embodiment of a capacitance-to-digital converter utilizing digital feedback and auxiliary capacitor DACs.

In order to improve the system illustrated in FIG. 1, FIG. 2 shows an embodiment of a capacitance-to-digital converter 200 that includes an ADC 201, digital feedback circuit 203, a capacitor bridge circuit 205, and auxiliary capacitor DACs 210 and 212. Each of the auxiliary capacitor DACs 210 and 212, have one or more unit capacitors of value $C_{dac}$. Instead of having the capacitance $C_{fb}$ and thus ADC 201, cover the full range of capacitive variation between $C_{sense}$ and $C_{offset}$, the auxiliary capacitor DACs 210 and 212 offset the difference in $C_{sense}$ and $C_{offset}$ capacitance values in the bridge circuit 205 so that ADC 201 sees no incoming current on average. If $C_{sense}$ varies due to a change in the sensed parameter, the ADC 201 sees error current at front-end integrator 206. The ADC 201 then adjusts the ADC output ds_out(t) 205 such that its effective averaged value becomes positive or negative (note that the ADC output ds_out(t) 205 is alternating between positive and negative values (for instance, +1 and −1) even when error is zero), which will be accumulated by the digital accumulator 211 in the digital feedback circuit 203. In an embodiment the ADC 201 is a second order sigma delta converter that includes the front-end integrator 206 and the remainder 208 of the ADC 201. In other embodiments, the order of the ADC may be different. The remainder of ADC 208 can include additional accumulators, feedback paths, feedforward paths, and quantization. For example, while not shown in the figure, the input of the ADC 201 can be supplied in a feedforward path to be utilized by the remainder of the ADC 208. The details of the front-end integrator of FIGS. 1 and 2 are shown to explain the use of chopping (which is needed for the chopped bridge structure that is utilized in order to rectify the signal corresponding to the capacitor bridge error), but the overall ADC 201 is not shown in detail since the ADC can be implemented using any commonly known discrete-time, switched capacitor topology. Note also, there are other ways of setting up the switches to achieve the desired chopping behavior, and FIGS. 1 and 2 are only examples of how to achieve the desired chopping. Note also that while two sense capacitors and two reference capacitors are shown in FIG. 2, other embodiment may have other numbers of capacitors. For example, an embodiment may utilize one sense capacitor and one reference capacitor to realize a single-ended implementation. Another embodiment may utilize one sense capacitor and three reference capacitors to realize a differential implementation in which only one side of the bridge contains the sense capacitor. In embodiments with one sense capacitor, only a single feedback capacitor and a single auxiliary capacitor DAC may be required, though additional calibration DACs may be utilized as well.

In the embodiment illustrated in FIG. 2, the digital feedback circuit 203, supplies the output 207 of the capacitance-to-digital converter 200 that corresponds to the sensed parameter. The input to be sensed, reflected in the $C_{sense}$ capacitance, is tracked by the auxiliary DACs 210 and 212 as controlled by the digital feedback path 203. The input tracking is aided by the fact that infinite DC gain is achieved by the digital accumulator used within the digital feedback path. The auxiliary capacitor DACs 210 and 212, rather than feedback capacitors, $C_{fb}$, cancel out, on average, the rectified bridge charge, $\Delta Q$. Therefore, the ADC 201 needs only to process the residual error and operates at a fixed DC operating point (nominally the mid-point of the ADC range, which typically corresponds to having an average output of value zero assuming instantaneous ADC output values of +1 and −1). The ADC 201 still controls the feedback capacitors $C_{fb}$, but the rectified charge created by the capacitance $C_{fb}$ corresponds to the residual error caused by incomplete cancellation of the bridge charge by the capacitor DACs, and this residual error has an average value of zero.

In contrast, FIG. 1 corresponds to the case where $C_f$ is added on average to $C_{sense}$ or $C_{offset}$ in proportion to the capacitor difference between $C_{sense}$ and $C_{offset}$ and therefore the code coming out of the sigma delta modulator of ADC 101 represents the capacitance difference between $C_{sense}$ and $C_{offset}$. In the embodiment of FIG. 1, $C_f$ has to be large enough to cover full range of capacitive difference between $C_{sense}$ and $C_{offset}$.

Referring again to FIG. 2, since the ADC 201 only needs to process a residual error signal, the value of $C_f$ can be reduced since the range of the residual error signal is considerably smaller than that of the signal (i.e. the bridge transfer charge $\Delta Q$ which would vary according to the difference between $C_{sense}$ and $C_{offset}$ in the absence of the feedback from $C_{fb}$ and $C_{dac}$). In an embodiment, the value of $C_{fb}$ is set to approximately twice the $C_{dac}$ unit value, though the optimal ratio of $C_{fb}$ to the unit $C_{dac}$ value may vary across different applications. That implies that the value of $C_{fb}$ is reduced as the number of $C_{dac}$ units, labeled as N in FIG. 2, is increased. For many applications, a practical value of N is in the range of 15 to 31, which implies a decrease in the value of $C_{fb}$ by a factor of 8 to 16 as compared to the feedback capacitance $C_f$ of FIG. 1. The resulting reduction of $C_{fb}$ and unit value of $C_{dac}$ lead to dramatically reduced quantization noise from the ADC, which, in turn, reduces the output range required of the front-end integrator 206 given a fixed value of $C_{int}$ and also reduces sensitivity to the nonlinear characteristic of the analog amplifier 214 in the front-end integrator 206. The reduced output range required of the output integrator allows a smaller $C_{int}$ capacitor to be used, thereby saving area in the ADC.

For ADCs, overall open loop DC gain typically limits resolution of the ADC. If the error to be sensed is small enough that amplifying it through stages does not produce a measurable error signal then that error cannot be sensed anymore. If high signal to noise ratio (SNR) is desired out of the ADC, then it is necessary to have very high open loop DC gain. For the ADC of FIG. 1, Cf sets the full scale range and the amount of open loop DC gain limits the achievable resolution within that range. However, in the embodiment of FIG. 2 an important benefit of the digital path is that the accumulator offers infinite DC gain, thus allowing infinite DC gain for the overall feedback loop.

Referring still to FIG. 2, the digital feedback circuit 203 includes fast settling logic 209 that nominally passes the output 205 of the ADC 201 into the digital accumulator 211. However, if a prescribed number of consecutive bits (such as 10 bits of the same value) is seen from the ADC output, which implies saturation of the ADC, then a large value is sent into the digital accumulator 211 to cause it to take a larger step size in the appropriate direction in order to improve settling time of the capacitor-to-digital converter. The sign of the step is determined based on whether the consecutive bits are high or low, and setting a minimum delay between steps insures that the ADC can properly settle after each step before checking for the consecutive bit condition.

The digital accumulator 211 accumulates the digitized residual error signal from the ADC, and the accumulated residual error signal is used to create the auxiliary DAC input signal. The digital accumulator always holds its information until the digital accumulator is told to go up or down due to a change in $C_{sense}$. The infinite DC gain of the accumulator forces the digitized residual error of capacitor bridge 205 to have an average value of zero, thereby maintaining a fixed DC operating point for the ADC 201. If an error current occurs because $C_{sense}$ changes, that error gets manifested as a non-zero average coming from ADC 201. That error gets accumulated in digital accumulator 211, which is used to adjust the auxiliary capacitor DACs 210 and 212 until the residual error of capacitor bridge 205 as offset by the capacitor DACs, is zero, in which case the ADC 201 input becomes zero (e.g., typically the mid point of its range) and the average of its output that is supplied to the digital accumulator 211 becomes zero. In contrast, for the embodiment of FIG. 1, the operating point of the ADC 201 must change according to the difference in capacitance between $C_{sense}$ and $C_{offset}$ since control of the capacitance $C_f$ must compensate for the capacitor difference between $C_{sense}$ and $C_{offset}$ rather than, for the embodiment of FIG. 2, a residual error whose average value of zero. The accumulator 211 functions to decouple the DC operating point of the ADC from the difference between $C_{sense}$ and $C_{offset}$ and the digital accumulator output becomes the basis for the overall output 207 of the system 200.

The digital low pass filter 215 receives the output of the digital accumulator 211 and further reduces ADC quantization noise. In an embodiment, a first order low pass filter topology is sufficient assuming that the ADC provides second order shaping of its quantization noise.

The digital delta sigma modulator 217 quantizes the signal from the digital low pass filter 215 according to the number of elements used in the auxiliary capacitor DAC. A second order multi-bit topology may be preferred to minimize the number of levels required for quantization noise (which reduces the effective range of the DAC) while achieving well behaved quantization noise (for which higher order is better).

The dynamic element matching (DEM) logic 219 accounts for mismatch of the units cells of the capacitor DACs 210 and 212 and may utilize Data Weighted Averaging or other techniques to shape the impact of mismatch of the DAC capacitive elements to higher frequencies. The output 220 of the DEM logic 219 controls the elements of the $C_{dac}$ 210 and $C_{dac}$ 212. Note that while $C_{dac}$ 212 receives the N bit output 220 of the DEM logic 210, $C_{dac}$ 210 receives the inverted N bit output 222 from inverter 221. In FIG. 2, it is implicitly assumed that a binary to thermometer conversion takes place on the digital Delta Sigma output that is received by the DEM logic.

In operation, elements of $C_{dac}$ 212 are selectively coupled to the voltage on node 230 or 232 through switch 233, which is controlled by the N bit output 220. Similarly, the elements of $C_{dac}$ 210 are selectively coupled to the voltage on node 230 or 232 based on the switch 234 controlled by the N bit output 222. Switch 241 couples node 230 to either Vrefp or Vrefm based on the clock signal 243. Switch 251 selectively couples node 232 to Vrefp or Vrefm based on clock signal 253, which is the inverse of clock signal 243.

The digital accumulate and dump circuit 260 filters noise and provides a decimated output. The accumulate and dump circuit 260 effectively averages a number of samples of the capacitance-to-digital converter. In an embodiment, the accumulate and dump circuit provides a scaled average of N samples at a time by accumulating over the full number of samples that occurred during the chosen measurement time frame (N samples) and then "dumping" the resulting value. In an embodiment N is 512. Other values of N are of course possible. Alternatively, the capacitance-to-digital converter could be run for N cycles, e.g., 512 cycles, and then output the resulting digitized signal. The output provided by the digital accumulate and dump circuit 260 may be viewed as a scaled average, where the scale factor may correspond to the number of samples accumulated. However, the scale factor could be modified using appropriate digital logic according to system requirements of various embodiments. For example, the scaling factor may be one, greater than one, or less than one.

At the beginning of a parameter measurement, e.g., when the system is first turned on, or when the system first takes a measurement, it can take time for the digital accumulator 211 to settle before the auxiliary capacitor DACs 210 and 212 are at the right value. For example, the settling time can be 10 percent of the chosen measurement time frame (e.g., 512 clk$_{ds}$ samples), where clk$_{ds}$ has a period of T$_{ds}$. So if the settling time is 10 percent of the number of samples, the capacitive-to-digital converter should be operated with measurement time frame that is roughly 10% longer than its steady-state measurement time frame and the digital accumulate and dump circuit should operate only on samples that occur after the initial settling time. Having a high oversampling rate (OSR), helps make the settling time more acceptable since the high OSR reduces the relative amount of time devoted to settling as compared to lower OSRs. Note that this issue occurs primarily for applications that only need an occasional measurement of the parameter. In cases where continuous capacitance-to-digital operation is desired, only the initial measurement time frame must be extended in time due to the initial settling issue, with remaining measurement samples simply utilizing the steady-state measurement time frame.

Thus, various aspects of capacitance-to-digital conversion have been described. The description of the invention set forth herein is illustrative, and is not intended to limit the scope of the invention as set forth in the following claims. Other variations and modifications of the embodiments disclosed herein, may be made based on the description set forth herein, without departing from the scope of the invention as set forth in the following claims.

What is claimed is:

1. A capacitance-to-digital converter circuit comprising:
   a capacitor bridge circuit to sense a difference in capacitance between one or more sense capacitors and other capacitors in the bridge circuit;
   auxiliary capacitor digital to analog converters (DACs) coupled to the capacitor bridge circuit to reduce a magnitude of an error signal corresponding to the sensed difference;
   an analog to digital converter (ADC) coupled to the capacitor bridge circuit and the auxiliary capacitor DACs to convert the error signal whose magnitude is reduced by the auxiliary capacitor DACs to a digital signal;
   a digital accumulator coupled to the ADC to accumulate the digital signal from the ADC; and
   wherein the auxiliary capacitor DACs are controlled to offset the difference in capacitance between the one or more sense capacitors and the other capacitors in the bridge circuit based on the accumulated digital signal.

2. The capacitance-to-digital converter circuit as recited in claim 1 wherein the one or more sense capacitors are responsive to change in capacitance in accordance with change in a sensed parameter.

3. The capacitance-to-digital converter circuit as recited in claim 1 further comprising a feedback capacitance circuit coupled to the bridge circuit and controlled by the digital signal from the ADC to cancel a residual error caused by incomplete cancellation by the auxiliary capacitor DACs of the difference in capacitance between the sense capacitors and the other capacitors in the bridge circuit.

4. The capacitance-to-digital converter circuit as recited in claim 3 wherein the feedback capacitance circuit comprises a first feedback capacitance selectively coupled to a first node of the capacitor bridge circuit according to a first value of the digital signal and coupled to a second node of the capacitor bridge circuit according to a second value of the digital signal and wherein the feedback capacitance circuit further comprises a second feedback capacitance selectively coupled to the second node of the capacitor bridge circuit according to the first value of the digital signal and coupled to the first node of the capacitor bridge circuit according to the second value of the digital signal.

5. The capacitance-to-digital converter circuit as recited in claim 1 wherein a first of the auxiliary capacitor DACs comprises a first plurality of unit capacitors selectively coupled to a first node or a second node of the capacitor bridge circuit based on the accumulated digital signal and wherein a second of the auxiliary capacitor DACs comprises a second plurality of unit capacitors selectively coupled to the second node or the first node of the capacitor bridge circuit according to the accumulated digital signal.

6. The capacitance-to-digital converter circuit as recited in claim 4 further comprising a digital control circuit to provide control signals to the auxiliary DACs, the digital control circuit-including the digital accumulator, the digital control circuit further including a digital delta sigma modulator coupled to receive the accumulated digital signal from the digital accumulator.

7. The capacitance-to-digital converter circuit as recited in claim 1 wherein the accumulated digital signal corresponds to the difference in capacitance between the one or more sense capacitors and the other capacitors in the bridge circuit.

8. The capacitance-to-digital converter circuit as recited in claim 1 further comprising a digital control circuit including the digital accumulator, and wherein the digital control circuit further comprises fast settling logic coupled to receive the digital signal from the ADC and responsive to a predetermined number of consecutive bits of the digital signal having an equal value, to supply a step value to the digital accumulator to improve settling time of the capacitance-to-digital converter.

9. The capacitance-to-digital converter circuit as recited in claim 1 further comprising a digital control circuit including the digital accumulator, and wherein the digital control circuit further comprises a digital accumulate and dump circuit coupled to the digital accumulator to compute a scaled average of a predetermined number of samples of the digital accumulator and provide the scaled average as an output signal, the output signal corresponding to the difference in capacitance between the one or more sense capacitors and the other capacitors in the bridge circuit.

10. The capacitance-to-digital converter circuit as recited in claim 3 further comprising an analog integrator circuit including an amplifier and switched capacitors coupled to the bridge circuit to rectify and accumulate the error signal generated by the capacitor bridge circuit and the feedback capacitance circuit and the auxiliary capacitor DACs and wherein the analog integrator circuit forms part of the ADC.

11. The capacitance-to-digital converter circuit as recited in claim 10 wherein the ADC corresponds to a delta sigma modulator.

12. The capacitance-to-digital converter circuit as recited in claim 10 wherein the capacitor bridge circuit further comprises a first switch to couple a first node of the capacitor bridge circuit to one of a first and second reference voltages according to a first clock signal and a second switch to couple a second node of the capacitor bridge circuit to one of the second and the first reference voltages according to a second clock signal, the second clock signal being an inverse of the first clock signal, and wherein a third node of the capacitor bridge circuit is coupled to a first input of the amplifier and is coupled to one of the switched capacitors and a fourth node of the capacitor bridge circuit is coupled to a second input of the amplifier and is coupled to another one of the switched capacitors.

13. A method comprising:
sensing a difference in capacitance between one or more sense capacitors and other capacitors in a capacitor bridge circuit;
offsetting the sensed difference using auxiliary capacitor digital-to-analog converters (DACs) coupled to the bridge circuit to generate a remaining sensed difference;
converting the remaining sensed difference to a digital signal using an analog-to-digital converter (ADC);
accumulating the digital signal using a digital accumulator, the accumulated digital signal corresponding to the sensed difference between the one or more sense capacitors and the other capacitors; and
controlling the auxiliary capacitor digital-to-analog converters (DACs) based on the accumulated digital signal.

14. The method as recited in claim 13 further comprising canceling a difference in capacitance between the sense capacitors and the other capacitors in the bridge circuit using the auxiliary capacitor DACs.

15. The method as recited in claim 14 further comprising:
controlling a feedback capacitor circuit coupled to the bridge circuit using the digital signal to cancel a residual error caused by incomplete cancellation by the auxiliary capacitor DACs of the difference in capacitance between the one or more sense capacitors and the other capacitors in the bridge circuit.

16. The method as recited in claim 14 further comprising using a digital delta sigma modulator coupled to the digital accumulator to generate signals for use in controlling the auxiliary capacitor DACs.

17. The method as recited in claim 13 further comprising generating a scaled average of a predetermined number of samples based on the digital accumulator and providing the scaled average as an output signal corresponding to the difference in capacitance between the one or more sense capacitors and the other capacitors in the bridge circuit.

18. The method as recited in claim 13 further comprising accumulating the signal supplied from the bridge circuit as offset by the auxiliary capacitor DACs using an analog integrator circuit of the ADC, the analog integrator circuit including an amplifier and switched capacitors coupled to the bridge circuit.

19. A capacitance-to-digital converter comprising:
a capacitor bridge circuit including one or more first capacitors that vary according to a sensed parameter and second capacitors, the bridge circuit creating an error signal corresponding to a difference in capacitance between the one or more first capacitors and the second capacitors;
one or more auxiliary capacitor digital-to-analog converters (DACs) coupled to the capacitor bridge circuit to offset the difference in capacitance sensed by the capacitor bridge circuit;
an analog-to-digital converter (ADC) coupled to the capacitor bridge circuit to supply a digital signal corresponding to the difference in capacitance sensed by the capacitor bridge circuit as offset by the one or more auxiliary capacitor DACs;
a feedback capacitance coupled to the digital signal from the ADC to the capacitor bridge circuit to cancel a residual error caused by incomplete cancellation by the one or more auxiliary capacitor DACs of the difference in capacitance between the one or more first capacitors and the second capacitors in the bridge circuit;
a digital feedback circuit that includes a digital accumulator to accumulate the difference in capacitance sensed by the capacitor bridge circuit as offset by the one or more auxiliary capacitor DACs and supply an accumulated signal indicative thereof, the accumulated signal corresponding to the difference in capacitance between the one or more first capacitors and the second capacitors; and
wherein the digital feedback circuit is further configured to control the one or more auxiliary capacitor DACs to offset the difference in capacitance between the one or more first capacitors and the second capacitors based on the accumulated signal; and
wherein the digital feedback circuit is further configured to supply an output of the capacitance-to-digital converter based on the accumulated signal.

20. The capacitance-to-digital converter as recited in claim 19 wherein the digital feedback circuit further comprises a digital delta sigma modulator coupled to the digital accumulator and configured to supply an output for use in controlling the one or more auxiliary capacitor DACs.

21. The capacitance-to-digital converter as recited in claim 19 wherein the digital feedback circuit further comprises:
fast settling logic coupled to receive the digital signal from the ADC and responsive to a predetermined number of consecutive bits of the digital signal having an equal value, to supply a step value to the digital accumulator to improve settling time of the capacitance-to-digital converter; and
a digital accumulate and dump circuit coupled to the digital accumulator to compute a scaled average of a predetermined number of samples of the digital accumulator and provide the scaled average as an output signal of the capacitance-to-digital-converter, the output signal corresponding to the difference in capacitance between the one or more first capacitors and the second capacitors in the bridge circuit.

* * * * *